(12) United States Patent
Schwab et al.

(10) Patent No.: US 7,485,692 B2
(45) Date of Patent: *Feb. 3, 2009

(54) PROCESS FOR ASSEMBLY OF POSS MONOMERS

(75) Inventors: Joseph J. Schwab, Huntington Beach, CA (US); Yi-Zhong An, Irvine, CA (US)

(73) Assignee: Hybrid Plastics, Inc., Hattiesburg, MS (US)

(*) Notice: Subject to any disclaimer, the term of this patent is extended or adjusted under 35 U.S.C. 154(b) by 131 days.

This patent is subject to a terminal disclaimer.

(21) Appl. No.: 11/371,195

(22) Filed: Mar. 7, 2006

(65) Prior Publication Data

US 2007/0232823 A1  Oct. 4, 2007

Related U.S. Application Data

(63) Continuation-in-part of application No. 11/225,607, filed on Sep. 12, 2005, which is a continuation-in-part of application No. 11/166,008, filed on Jun. 24, 2005, and a continuation-in-part of application No. 10/351,292, filed on Jan. 23, 2003, now Pat. No. 6,933,345, and a continuation-in-part of application No. 10/186,318, filed on Jun. 27, 2002, now Pat. No. 6,927,270, which is a continuation-in-part of application No. 09/818,265, filed on Mar. 26, 2001, now Pat. No. 6,716,919, and a continuation-in-part of application No. 09/747,762, filed on Dec. 21, 2000, now Pat. No. 6,911,518, which is a continuation-in-part of application No. 09/631,892, filed on Aug. 14, 2000, now Pat. No. 6,972,312.

(60) Provisional application No. 60/659,722, filed on Mar. 7, 2005, provisional application No. 60/608,582, filed on Sep. 10, 2004, provisional application No. 60/351,523, filed on Jan. 23, 2002, provisional application No. 60/301,544, filed on Jun. 27, 2001, provisional application No. 60/171,888, filed on Dec. 23, 1999, provisional application No. 60/147,435, filed on Aug. 4, 1999.

(51) Int. Cl.
*C08G 77/08* (2006.01)

(52) U.S. Cl. ....................................... 528/23

(58) Field of Classification Search .................. 528/23, 528/34
See application file for complete search history.

(56) References Cited

U.S. PATENT DOCUMENTS

| | | | |
|---|---|---|---|
| 2,801,968 A | 8/1957 | Furby et al. | |
| 3,231,499 A | 1/1966 | Smith | |
| 3,247,111 A | 4/1966 | Oberright et al. | |
| 3,278,436 A | 10/1966 | Dazzi | |
| 3,280,031 A | 10/1966 | Brennan et al. | |
| 3,292,180 A | 12/1966 | Axworthy | |
| 3,340,286 A | 9/1967 | Schiefer et al. | |
| 3,347,791 A | 10/1967 | Thomson et al. | |
| 3,390,163 A | 6/1968 | Brown | |
| 3,673,229 A | 6/1972 | Malec | |
| 4,483,107 A | 11/1984 | Tomoyori et al. | |
| 4,513,132 A | 4/1985 | Shoji et al. | |
| 4,900,779 A | 2/1990 | Liebfried | |
| 4,946,921 A | 8/1990 | Shirata et al. | |
| 5,047,491 A | 9/1991 | Saho et al. | |
| 5,047,492 A | 9/1991 | Weidner et al. | |
| 5,190,808 A | 3/1993 | Tenney et al. | |
| 5,412,053 A | 5/1995 | Lichtenhan et al. | |
| 5,457,220 A | 10/1995 | Razzano | |
| 5,484,867 A | 1/1996 | Lichtenhan et al. | |
| 5,589,562 A | 12/1996 | Lichtenhan et al. | |
| 5,830,950 A | 11/1998 | Katsoulis et al. | |
| 5,855,962 A | 1/1999 | Cote et al. | |
| 5,858,544 A | 1/1999 | Banaszak Holl et al. | |
| 5,939,576 A | 8/1999 | Lichtenhan et al. | |
| 5,942,638 A | 8/1999 | Lichtenhan et al. | |
| 6,075,068 A | 6/2000 | Bissinger | |
| 6,100,417 A | 8/2000 | Lichtenhan et al. | |
| 6,245,849 B1 | 6/2001 | Morales et al. | |
| 6,245,926 B1 | 6/2001 | Charrin et al. | |
| 6,252,030 B1 | 6/2001 | Zanket et al. | |
| 6,288,904 B1 | 9/2001 | Yadav et al. | |
| 6,329,490 B1 | 12/2001 | Yamashita et al. | |
| 6,596,821 B1 | 7/2003 | Katsoulis et al. | |
| 6,660,823 B1 | 12/2003 | Lichtenhan et al. | |
| 6,770,724 B1 | 8/2004 | Lichtenhan et al. | |
| 6,927,270 B2 | 8/2005 | Lichtenhan et al. | |
| 6,972,312 B1 | 12/2005 | Lichtenhan et al. | |
| 2003/0055193 A1* | 3/2003 | Lichtenhan et al. | 528/10 |

OTHER PUBLICATIONS

Billmeyer, *Textbook of Polymer Science*, 3rd ed., Wiley & Sons, New York: New York, 1984, Chapter 6, pp. 471-472.

Chevaliaer & McKinnon, "Ring Opening Olefin Metathesis Polymerisation (ROMP) as a Potential Cross-Linking Mechanism for Siloxane Polymers", *J. of Inorganic and Organometallic Polymers*, 9:3, 1999.

Marsmann, et al., "Cage Rearrangement of Silsequioxanes", *Polyhedron*, 16:19, pp. 3357-3361, 1997.

\* cited by examiner

*Primary Examiner*—Kuo-Liang Peng
(74) *Attorney, Agent, or Firm*—David H. Jaffer; Pillsbury Winthrop Shaw Pittman LLP

(57) ABSTRACT

A synthesis process for polyhedral oligomeric silsesquioxanes using phosphazene superbases to produce in high yield a low resin content, solvent free, and trace metal free monomer suitable for use in microelectronic, biological, and medical applications involving polymerization, grafting, and alloying.

12 Claims, 3 Drawing Sheets

PROCESS FOR ASSEMBLY OF POSS MONOMERS

CROSS-REFERENCE TO RELATED APPLICATIONS AND PATENTS

This application claims priority from U.S. Provisional Patent Application Ser. No. 60/659,722 Filed Mar. 7, 2005, and is a continuation-in-part of U.S. patent application Ser. No. 11/225,607 filed Sep. 12, 2005 (which claims priority from U.S. Provisional Patent Application Ser. No. 60/608,582 filed Sep. 10, 2004), which is a continuation-in-part of U.S. patent application Ser. No. 11/166,008 filed Jun. 24, 2005, which is (a) a continuation-in-part of U.S. patent application Ser. No. 09/631,892 filed Aug. 14, 2000, now U.S. Pat. No. 6,972,312 (which claims priority from U.S. Provisional Patent Application Ser. No. 60/147,435, filed Aug. 4, 1999); (b) a continuation-in-part of U.S. patent application Ser. No. 10/351,292, filed Jan. 23, 2003, now U.S. Patent No. 6,933,345 (which claims priority from U.S. Provisional Patent Application Ser. No. 60/351,523, filed Jan. 23, 2002), which is a continuation-in-part of U.S. patent application Ser. No. 09/818,265, filed Mar. 26, 2001, now U.S. Pat, No. 6,716,919 (which claims priority from U.S. Provisional Patent Application Ser. No. 60/192,083, filed Mar. 24, 2000); (c) a continuation-in-part of U.S. patent application Ser. No. 09/747,762, filed Dec. 21, 2000, now U.S. Pat. No. 6,911,518 (which claims priority from U.S. Provisional Patent Application Ser. No. 60/171,888, filed Dec. 23, 1999); and (d) a continuation-in-part of U.S. patent application Ser. No. 10/186,318, filed Jun. 27, 2002, now U.S. Pat. No. 6,927,270 (which claims priority from U.S. Provisional Patent Application Ser. No. 60/301,544, filed Jun. 27, 2001).

FIELD OF THE INVENTION

This invention relates generally to a process for enhancing the properties of functionalized POSS monomers for incorporation into polymeric and biological products.

BACKGROUND OF THE INVENTION

Nanostructured chemicals are best exemplified by those based on low-cost Polyhedral Oligomeric Silsesquioxanes (POSS) and Polyhedral Oligomeric Silicates (POS). POSS systems contain hybrid (i.e. organic-inorganic) compositions in which the internal cage like framework is primarily comprised of inorganic silicon-oxygen bonds. The exterior of the nanostructure is covered by both reactive and nonreactive organic functionalities (R), which ensure compatibility and tailorability of the nanostructure with organic monomers and polymers. These and other properties and features of nano-structured chemicals are discussed in detail in U.S. Pat. No. 5,412,053 and U.S. Pat. No. 5,484,867, both of which are expressly incorporated herein by reference in their entirety.

Current-engineering practices produce functionalized POSS molecules in high yield but certain microelectronic, medical, and biological applications require higher-purity or chemical functionalities that are not readily or economically produced using the prior art. Prior art methods include the use of hydroxide base, anionic salts, and protic, acid catalysts in the assembly of POSS cages and their functionalization (see U.S. patent application Ser. Nos. 09/631,892 and 10/186,318, and U.S. Pat. Nos. 6,770,724; 6,660,823; 6,596,821; and 3,390,163). While these approaches are known to be generally effective, they are limited in that both protic acids and hydroxide bases can also catalyze the self-condensation of POSS individual cages into oligomerized POSS cage containing resins (FIG. 1). Such resins are not desirable in microelectronics, biological or medical applications, as their structure is molecularly imprecise. Furthermore, the dispersion of the POSS molecules and their compatibility with polymers is thermodynamically governed by the free energy of mixing equation ($\Delta G = \Delta H - T\Delta S$). The nature of the R group and ability of the reactive groups on the POSS cage to react or interact with polymers and surfaces greatly contributes to a favorable enthalpic ($\Delta H$) term while the entropic term ($\Delta S$) for POSS is highly favorable when the cage size is monoscopic and the corresponding distribution of oligomers is 1.0.

Consequently a need exists for improvement upon the prior art methods of POSS cage assembly and functionalized monomers. An improved process yielding, higher purity, and molecularly precise POSS systems is described.

SUMMARY OF THE INVENTION

The present invention provides an improved synthesis process for polyhedral oligomeric silsesquioxanes which produces rapidly, in high yield, low resin content, and solvent free, monomer products suitable for use in polymerization, grafting and alloying applications. The synthesis process uses phosphazene superbases in reaction with silane coupling agents of the formula $R^1SiX_3$ to form POSS cages functionalized with silanols of the formula types $[(R^1SiO_{1.5})_7(HOSiO_{1.5})_1]_{\Sigma 8}$, $[(R^1SiO_{1.5})_6(R^1HOSiO_1)_2]_{\Sigma 8}$, $[(R^1SiO_{1.5})_2(R^1HOSiO_1)_4]_{\Sigma 6}$, $[(R^1SiO_{1.5})_4(R^1HOSiO_1)_3]_{\Sigma 7}$. The synthesis process can also involve the reaction of phosphazene superbases in reaction with silane coupling agents of the type $R^2SiX_3$ to form polyfunctional POSS cages functionalized with $R^2$ groups of the formula types $[(R^2SiO_{1.5})_6]_{\Sigma 6}$, $[(R^2SiO_{1.5})_8]_{\Sigma 8}$, $[(R^2SiO_{1.5})_{10}]_{\Sigma 10}$, $[(R^2SiO_{1.5})_{12}]_{\Sigma 12}$ and larger sized cages.

Alternately the phosphazene superbases can be reacted with POSS silanols of the formula $[(R^1SiO_{1.5})_7(HOSiO_{1.5})_1]_{\Sigma 8}$, $[(R^1SiO_{1.5})_6(R^1HOSiO_1)_2]_{\Sigma 8}$, $[(R^1SiO_{1.5})_4(R^1HOSiO_1)_3]_{\Sigma 7}$ in the presence of a silane coupling agent of the formula $R^2R^3R^4SiX$, $R^2R^3SiX_2$, or $R^2SiX_3$ for sufficient time in the presence of a solvent and superbase where the elimination of HX occurs and renders a monofunctional POSS monomer of the formula $[(R^1SiO_{1.5})_8(R^2R^3R^4SiO_1)]_{\Sigma 9}$, $[((R^1SiO_{1.5})_8)_2(R^2R^3SiO_2)]_{\Sigma 17}$, $[((R^1SiO_{1.5})_8)_3(R^2SiO_3)]_{\Sigma 25}$, $[(R^1SiO_{1.5})_6(R^1SiO_{1.5})_2(R^2R^3R^4SiO)_2]_{\Sigma 10}$, $[(R^1SiO_{1.5})_6(R^1SiO_1)_2(R^2R^3SiO_2)]_{\Sigma 9}$, $[(R^1SiO_{1.5})_6(R^1HOSiO_1)_1(R^2R^3SiO)]_{\Sigma 8}$, $[(R^1SiO_{1.5})_6(R^1(R^2R^3R^4SiO)SiO_1)(R^2R^3SiO)]_{\Sigma 9}$, $[(R^1SiO_{1.5})_4(R^1(R^2R^3R^4SiO)SiO_1)_3]_{\Sigma 10}$, $[(R^1SiO_{1.5})_7(R^2SiO_{1.5})_1]_{\Sigma 8}$, respectively. The resulting monomer is essentially free of impurities and has controllable properties through selection of composition, R groups, and nanostructure size and topology. Highly purified nanostructured POSS monomers are desirable as they exhibit improved filtration capability, reduced contamination and viscosity, more reliable polymerization, lower cost and waste reduction over impure systems.

A preferred process involves the reaction of POSS silanols of the formula $[(R^1SiO_{1.5})_7(HOSiO_{1.5})_1]_{\Sigma 8}$, $[(R^1SiO_{1.5})_6(R^1HOSiO_1)_2]_{\Sigma 8}$, $[(R^1SiO_{1.5})_4(R^1HOSiO_1)_3]_{\Sigma 7}$ with a silane coupling agent of the formula, $R^2R^3R^4SiX$, $R^2R^3SiX_2$, $R^2SiX_3$ in the presence of a solvent and superbase.

DEFINITION OF FORMULA REPRESENTATIONS FOR NANOSTRUCTURES

Figure 1:
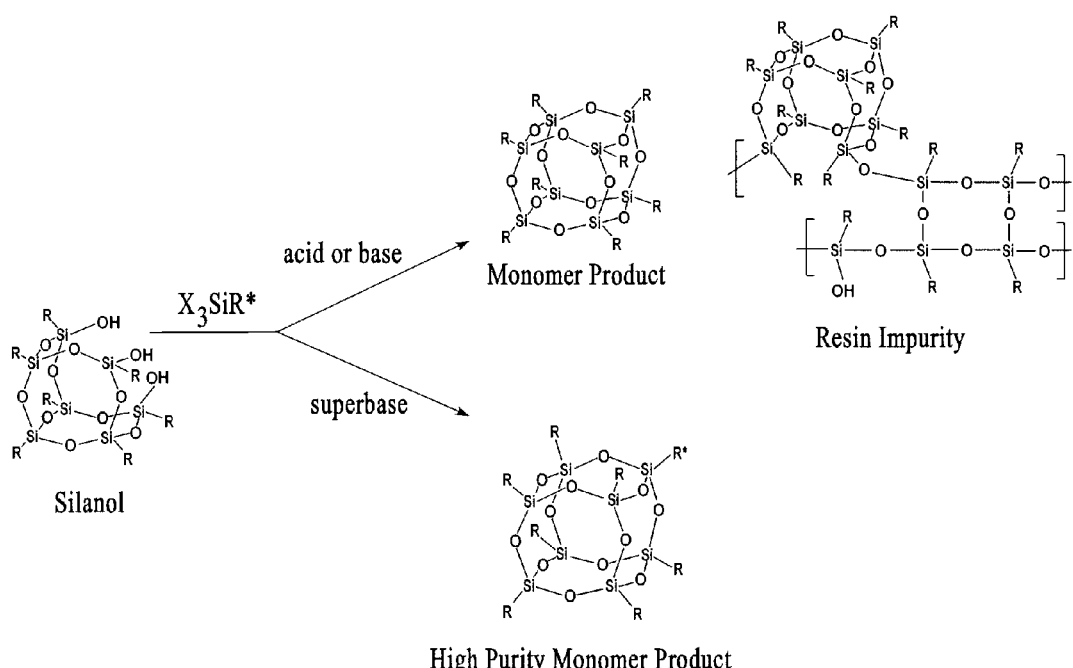
FIG. 1 shows a comparison of the prior art and improved silation process.
Figure 2:
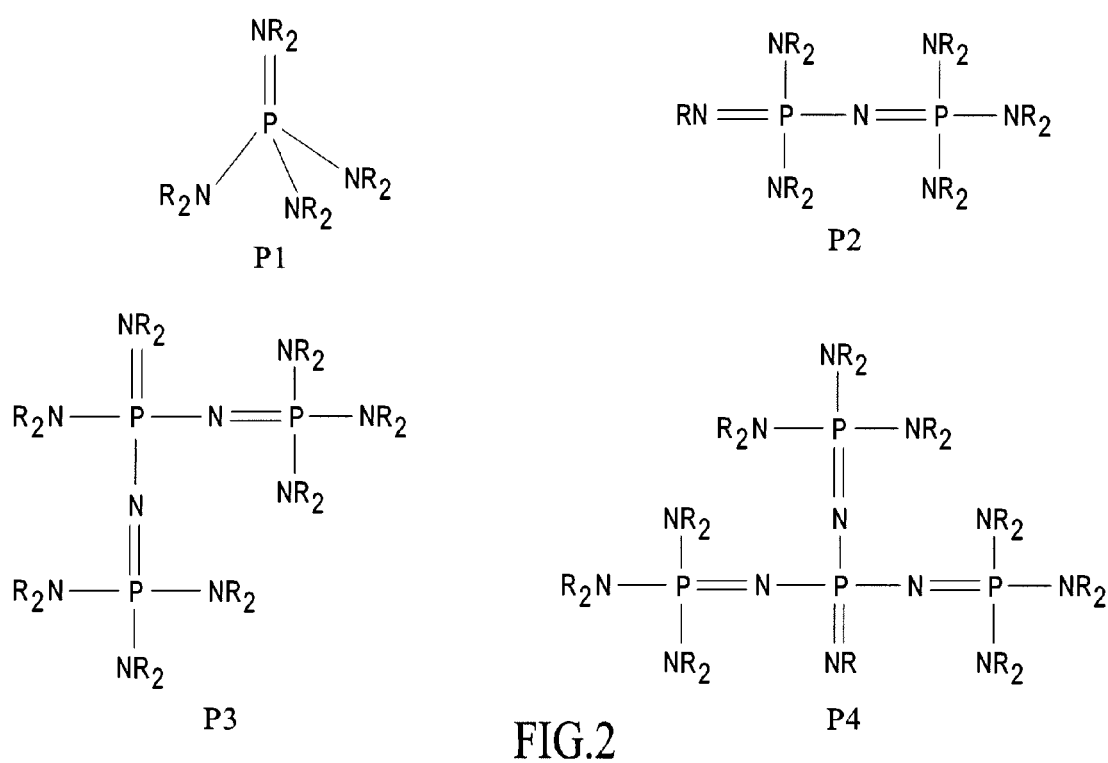
FIG. 2 shows a variety of the preferred phosphazene superbases.
Figure 3:
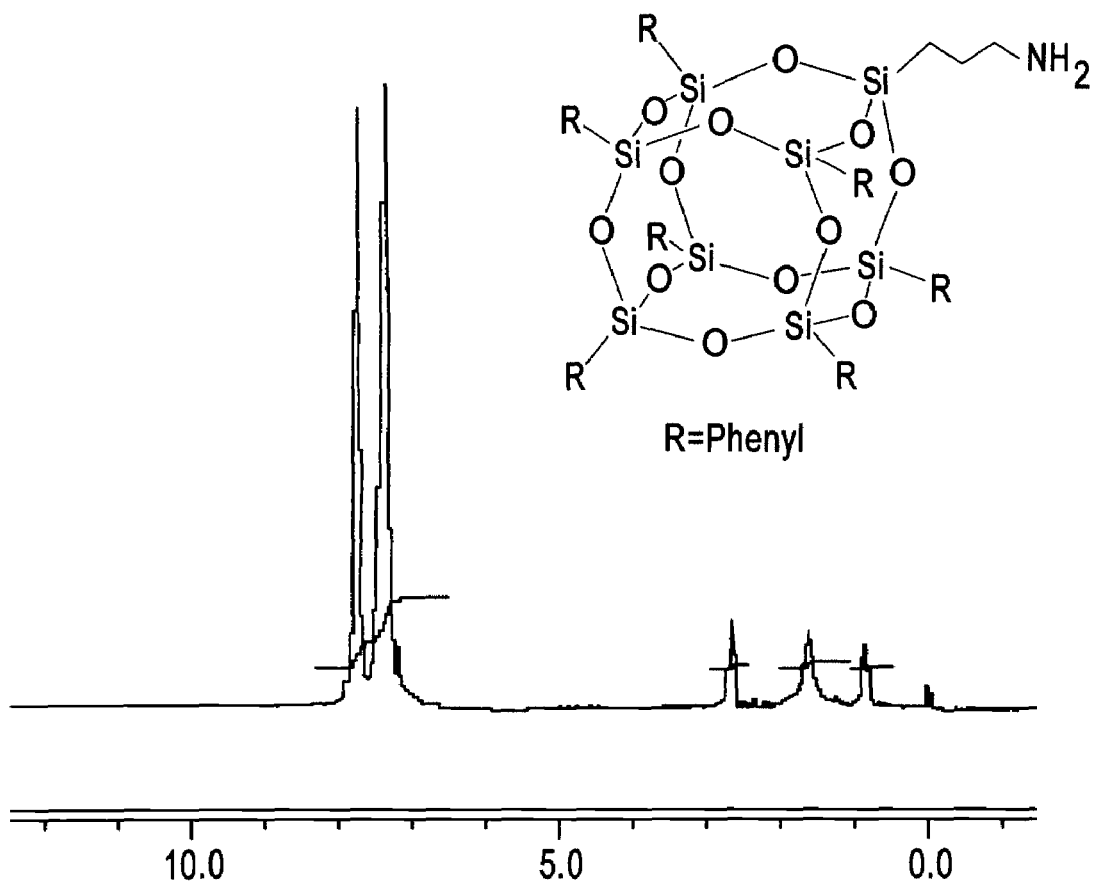
FIG. 3 shows the structure of the compound synthesized in Example 5.

For the purposes of understanding this invention's chemical compositions the following definition for formula representations of Polyhedral Oligomeric Silsesquioxane (POSS) and Polyhedral Oligomeric Silicate (POS) nanostructures is made.

Polysilsesquioxanes are materials represented by the formula $[RSiO_{1.5}]_\infty$ where $\infty$ represents molar degree of polymerization and R=represents organic substituent (H, siloxy, cyclic or linear aliphatic or aromatic groups that may additionally contain reactive functionalities such as alcohols, esters, amines, ketones, olefins, ethers or halides or which may contain fluorinated groups). Polysilsesquioxanes may be either homoleptic or heteroleptic. Homoleptic systems contain only one type of R group while heteroleptic systems contain more than one type of R group.

POSS and POS nanostructure compositions are represented by the formula:

$[(RSiO_{1.5})_n]_{\Sigma\#}$ for homoleptic compositions $[(RSiO_{1.5})_n(R'SiO_{1.5})_m]_{\Sigma\#}$ for heteroleptic compositions (where R≠R')

$[(RSiO_{1.5})_n(RXSiO_{1.0})_m]_{\Sigma\#}$ for functionalized heteroleptic compositions (where R groups can be equivalent or in equivalent)

In all of the above R is the same as defined above and X includes but is not limited to OH, Cl, Br, I, alkoxide (OR), formate (OCH), acetate (OCOR), acid (OCOH), ester (OCOR), peroxide (OOR), amine ($NR_2$) isocyanate (NCO), and R. The symbols m and n refer to the stoichiometry of the composition. The symbol $\Sigma$ indicates that the composition forms a nanostructure and the symbol # refers to the number of silicon atoms contained within the nanostructure. The value for # is usually the sum of m+n, where n ranges typically from 1 to 24 and m ranges typically from 1 to 12. It should be noted that $\Sigma\#$ is not to be confused as a multiplier for determining stoichiometry, as it merely describes the overall nanostructural characteristics of the system (aka cage size).

DETAILED DESCRIPTION OF THE INVENTION

The present invention teaches an improved method of synthesis for POSS nanostructured chemicals yielding a higher purity and lower cost product than previously described.

The key feature of the invention is the use of phosphazene superbases to catalyze the assembly of POSS cages. A range of phosphazenes are applicable and include polyphosphazenes which vary in molecular weight and composition. Phosphazene oligomers and molecules are preferentially utilized and in particular P1 type $P(NtBu)(NH_2)_3$, P2 type $(H_2N)_3P=N-P(NH_2)_4$, P3 type $(H_2N)_3P=N-P(NH_2)-N=P(NH_2)_3$, P4 type $(H_2N)_3P=N-P(NH_2)_3=N-P(NH_2)_3-N=P(NH_2)_3$. The basicity of phosphazene superbases increase with increasing number of phosphorous atoms and this provides a valuable tool in the utility of this reagent. The preferred concentration of superbase relative to trisilanol is 2 mol % but a useful range includes 0.1 mol % to 10 mol %.

General Process Variables Applicable To All Processes

As is typical with chemical processes there are a number of variables that can be used to control the purity, selectivity, rate and mechanism of any process. Variables influencing the process include the size, polydispersity, and composition of the nanostructured chemical, separation and isolation methods, and use of catalyst or cocatalysts, solvents and cosolvents. Additionally, kinetic and thermodynamic means of controlling the synthesis mechanism, rate, and product distribution are also known tools of the trade that can impact product quality and economics.

EXAMPLE 1

Synthesis of $[(isobutylSiO_{1.5})_7(methacrylpropylSiO_{1.0})_1]_{\Sigma 8}$ $[(isobutylSiO_{1.5})_4(isobutyl(OH)SiO_{1.0})_3]_{\Sigma 7}$ (688 g, 0.87 mole) was dissolved in THF followed by addition of methacrylpropyltrimethoxysilane (204 g, 0.87 mole) and the solution was cooled to 5° C. Phosphazene superbase (FW 234.32, 15.72 mmol) was then added and the mixture stirred at room temperature for 3 days. The solution was then quenched with acetic acid (1.5 g). Then 1 liter of methanol was added and the mixture was stirred and filtered. The solid was dried to render pure white product in 75% yield.

EXAMPLE 2

Synthesis of $[(EtSiO_{1.5})_7(glycidalSiO_{1.0})_1]_{\Sigma 8}$ $[(EtSiO_{1.5})_4(Et(OH)SiO_{1.0})_3]_{\Sigma 7}$ (50 g, 84 mmole) was dissolved in methanol followed by addition of 3-glycidoxypropyltrimethoxysilane (19.86 g, 84 mmole) and the solution was cooled to 5° C. Phosphazene superbase (FW 234.32, 15.72 mmol) was then added and the mixture stirred for 3 days at 5° C. The solution was then quenched with acetic acid (87 mg) filtered, and volatiles removed and dried to render a solid. The solid washed with methanol (1400 ml) and dried to render 415 g of pure white product in 87% yield.

EXAMPLE 3

Synthesis of $[(EtSiO_{1.5})_7(ethylnorborneneSiO_{1.0})_1]_{\Sigma 8}$ $[(EtSiO_{1.5})_4(Et(OH)SiO_{1.0})_3]_{\Sigma 7}$ (12 g, 20 mmole) was dissolved in methanol followed by addition of exo-norbornenylethyltrimethoxysilane (4.84 g, 20 mmole) and the solution was cooled to 5° C. Phosphazene superbase was then added and the mixture stirred for 2 days at 5° C. The solution was then quenched with acetic acid (87 mg) filtered, and volatiles removed, washed with additional methanol and dried to render a white product.

EXAMPLE 4

Synthesis of $[(CyclohexylSiO_{1.5})_7(aminoethylaminpropylSiO_{1.0})_1]_{\Sigma 8}$ $[(CyclohexylSiO_{1.5})_4(Cyclohexyl(OH)SiO_{1.0})_3]_{\Sigma 7}$ (10 g, 10.3 mmole) was dissolved in THF followed by addition of 3-(N-aminoethyl)aminopropyltrimethoxysilane (2.32 g, 10.27 mmole) and phosphazene superbase (FW 234.32, 15.72 mmol) was then added and the mixture stirred at room temperature. The solution was then quenched with acetic acid methanol was added. The volatiles were removed and product dried to render a pure white solid in 62% yield.

EXAMPLE 5

Synthesis of [(PhenylSiO$_{1.5}$)$_7$(aminopropyl SiO$_{1.0}$)$_1$]$_{\Sigma 8}$

[(PhenylSiO$_{1.5}$)$_4$(Phenyl(OH)SiO$_{1.0}$)$_3$]$_{\Sigma 7}$ (5.9 g, 6.3 mol) was dissolved in toluene followed by addition of (2.0 g, 11 mmol) 3-aminopropyltrimethoxysilane and was then stirred at room temperature for 12 hours. Acetonitrile was added and the solution was filtered and product dried to render a pure white solid in 40% yield.

While certain representative embodiments and details have been shown for purposes of illustrating the invention, it will be apparent to those skilled in the art that various changes in the methods and apparatus disclosed herein may be made without departing from the scope of the invention which is defined in the appended claims.

What is claimed is:

1. A method for preparing functionalized POSS monomers comprising the step of reacting a silane coupling agent having the formula RSiX$_3$ in the presence of a solvent and a phosphazene superbase, wherein:
   R is selected from the group consisting of hydrogen, siloxy, and aliphatic, aromatic, and olefinic groups, wherein said groups may contain reactive functionalities selected from the group consisting of alcohols, esters, amines, ketones, olefins, ethers, and halides, and may contain fluorinated subtituents;
   X is selected from the group consisting of OH, CI, Br, I, alkoxide (OR), formate, acetate (OCOR), acid (OCOH), ester (OCOR), peroxide (OOR), amine (NR$_2$), isocyanate (NCO), and R; and
   each R and each X may be the same or different.

2. The method of claim 1, wherein the superbase is selected from the group consisting of P1, P2, P3, and P4 type phosphazenes.

3. The method of claim 1, wherein a mixture of different silane coupling agents are reacted are utilized to prepare functionalized POSS monomers.

4. The method of claim 1, wherein a mixture of different superbases are utilized as homogeneous catalysts or coreagents.

5. The method of claim 1 wherein a mix of different solvents or reaction media are utilized.

6. The method of claim 1 wherein a continuous process rendering functionalized POSS monomers is utilized that uses the superbase as a heterogeneous catalyst or coreagent.

7. A method for preparing functionalized POSS monomers comprising the step of silating a POSS silanol with a silane coupling agent having the formula selected from the group consisting of RSiX$_3$, R$_2$SiX$_2$, and R$_3$SiX in the presence of a solvent and a phosphazene superbase, wherein:
   R is selected from the group consisting of hydrogen, siloxy, and aliphatic, aromatic, and olefinic groups, wherein said groups may contain reactive functionalities selected from the group consisting of alcohols, esters, amines, ketones, olefins, ethers, and halides, and may contain fluorinated substituents;
   X is selected from the group consisting of OH, CI, Br, I, alkoxide (OR), formate, acetate (OCOR), acid (OCOH), ester (OCOR), peroxide (OOR), amine (NR$_2$), isocyanate (NCO), and R; and
   each R and each X may be the same or different.

8. The method of claim 7, wherein the superbase is selected from the group consisting of P1, P2, P3, and P4 type phosphazenes.

9. The method of claim 7, wherein a mixture of different, POSS silanols and silane coupling agents are silated.

10. The method of claim 7, wherein a mixture of different superbases are utilized as homogeneous catalysts or coreagents.

11. The method of claim 7, wherein a mix of different solvents or reaction media are utilized.

12. The method of claim 7, wherein a continuous silation process is utilized that uses the superbase as a heterogeneous catalyst or coreagent.

* * * * *